United States Patent [19]

Singhal et al.

[11] Patent Number: 4,681,957

[45] Date of Patent: Jul. 21, 1987

[54] METHOD OF PREPARING HYDROCARBON SUBSTITUTED DITHIOCARBAMATES OF MOLYBDENUM

[75] Inventors: Gopal H. Singhal, Houston; Claude C. Culross, Baytown, both of Tex.

[73] Assignee: Exxon Research and Engineering Company, Florham Park, N.J.

[21] Appl. No.: 771,865

[22] Filed: Sep. 3, 1985

[51] Int. Cl.$^4$ ............................................ C07F 11/00
[52] U.S. Cl. ..................................................... 556/38
[58] Field of Search ......................................... 556/38

[56] References Cited

U.S. PATENT DOCUMENTS

| | | | |
|---|---|---|---|
| 3,356,702 | 12/1967 | Farmer et al. | 556/38 |
| 3,419,589 | 12/1968 | Larsen et al. | |
| 4,098,705 | 7/1978 | Sakurai et al. | 556/38 X |
| 4,588,829 | 5/1986 | Pan et al. | 556/38 |

FOREIGN PATENT DOCUMENTS

| | | | |
|---|---|---|---|
| 133309 | 12/1974 | Japan | 556/38 |
| 80825 | 7/1976 | Japan | 556/38 |

OTHER PUBLICATIONS

Moore and Larsen, Inorganic Chemistry, vol. 6, No. 5, May, 1967, pp. 998–1003.

R. N. Jowitt and P. C. M. Mitchell, J. Chem. Soc. (A), 1702–1708 (1970).

Pandeya and Kaul, Synth. React. Inorga. Met.-Org. Chem., 12 (3), 259–268, (1982).

*Primary Examiner*—Helen M. S. Sneed
*Attorney, Agent, or Firm*—Wayne Hoover

[57] ABSTRACT

An improved process for preparing dihydrocarbyl substituted dithiocarbamates of molybdenum wherein an alkali metal hydroxide is reacted with a mixture of a dihydrocarbyl substituted amine and carbon disulfide in an aqueous solution to produce an alkali metal salt of dithiocarbamate and the alkali metal salt then reacted with an alkali metal molybdate in the presence of acid to produce the dihydrocarbyl substituted dithiocarbamate of molybdenum. The process is completed in an inert atmosphere and within a relatively narrow range of temperatures so as to avoid the production of by-products which have heretofore reduced both the yield and purity of the final product. The preparation of the alkali metal salt of dithiocarbamate is completed at a temperature generally within the range from about −5 to about 30° C. The acidification of the alkali metal salt of dithiocarbamate is completed, generally, at a temperature within the range from about −5 to about 5° C.

5 Claims, 1 Drawing Figure

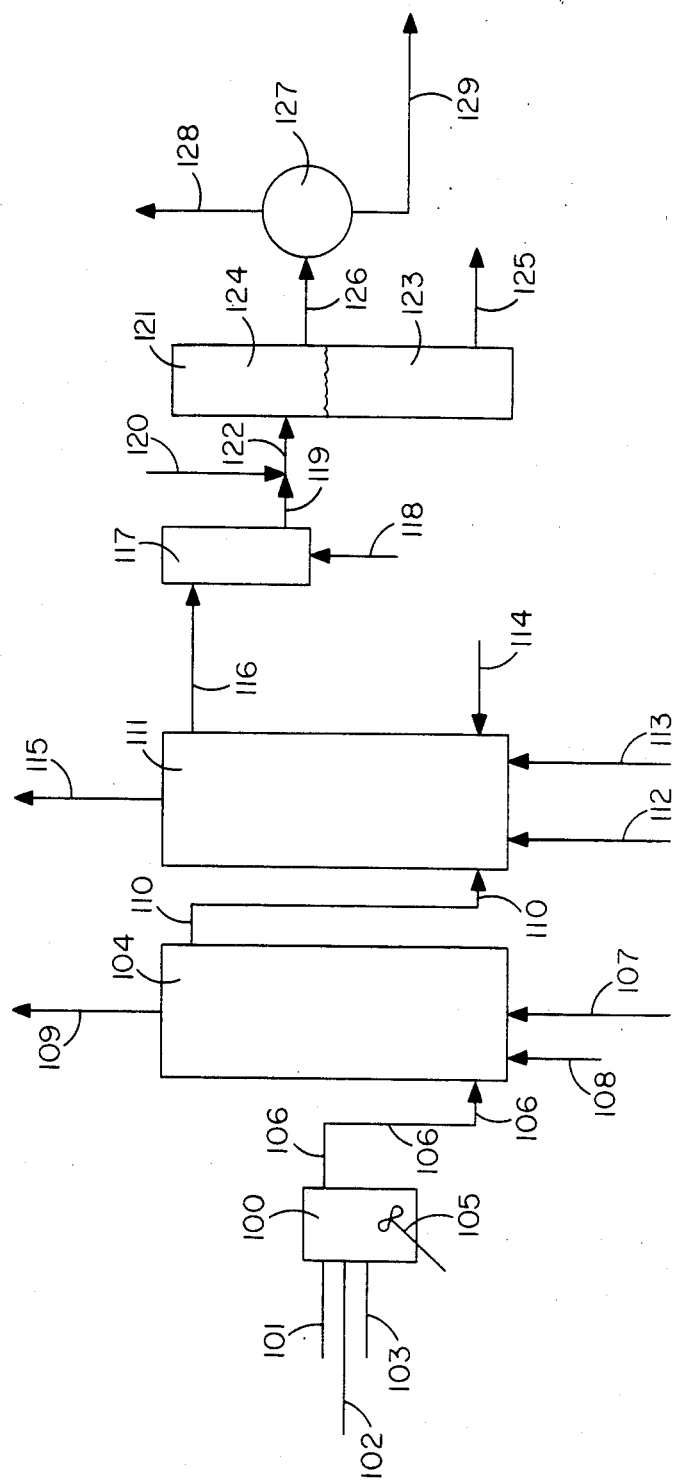
FIGURE

METHOD OF PREPARING HYDROCARBON SUBSTITUTED DITHIOCARBAMATES OF MOLYBDENUM

BACKGROUND OF THE INVENTION

This invention relates to a method for preparing metal organic compounds. More particularly, this invention relates to a method of preparing hydrocarbon substituted dithiocarbamates of molybdenum.

Processes for preparing hydrocarbon substituted dithiocarbamates of molybdenum have been proposed heretofore. In one such process, stoichiometric quantities of ammonium hydroxide, a dihydrocarbyl substituted amine and carbon disulfide are combined in water to produce a dihydocarbyl substituted alkali metal salt of a dithiocarbamate. The dihydrocarbyl substituted sodium salt of dithiocarbamate is then reacted with an alkali metal molybdate in the presence of acid to produce monomers and dimers of a dihydrocarbyl substituted dithiocarbamate of molybdenum. In general, the alkali metal molybdate is used at a concentration within the range from about 1.5 to about 2 moles per mole of alkali metal salt of a dithiocarbamate. The dimer produced during the acidification may be oxidized back to the monomer with a suitable oxidizing agent such as a peroxide or hydroperoxide. When an oxidizing agent is used, it is, generally, used in an amount ranging from about 0.2 to about 0.5 moles per mole of total molybdenum present in the reaction mixture.

While the process thus described has been effective in the production of dihydrocarbyl substituted dithiocarbamates of molybdenum, the product generally contains significant quantities of impurities (by-products) such as tetralkylthiouran disulfide, polysulfides and tars, which by-products lead to a reduced purity and yield. Since certain of these impurities are not easily separated from the product, thereby detracting from its ultimate final use, and since the yield resulting from this process is, generally, less than normally desired in a chemical process, the need for an improved process for the production of dihydrocarbyl substituted dithiocarbamates of molybdenum is believed to be readily apparent.

SUMMARY OF THE INVENTION

It has now been discovered that the foregoing and other disadvantages of the prior art processes for the production of dihydrocarbyl substituted dithiocarbamates of molybdenum can be avoided, or at least reduced, with the method of the present invention and an improved process for preparing such compounds provided thereby. It is therefore, an object of this invention to provide an improved process for the preparation of dihydrocarbyl substituted dithiocarbamates of molybdenum. It is another object of this invention to provide such a process wherein the amount of impurities produced is reduced. It is still a further object of this invention to provide such an improved process wherein the yield of dihydrocarbyl substituted dithiocarbamate of molybdenum is increased. It is yet another object of this invention to provide such a process wherein the purity of the dihydrocarbyl substituted dithiocarbamate of molybdenum is improved. The foregoing and other objects and advantages will become apparent from the description set forth hereinafter and from the drawing appended thereto.

In accordance with the present invention, the foregoing and other objects and advantages are accomplished by first combining the dihydrocarbyl substituted amine and the carbon disulfide and thereafter adding the alkali metal hydroxide to produce the alkali metal salt of the dihydrocarbyl substituted dithiocarbamate. The alkali metal salt of the dihydrocarbyl substituted amine is then acidified in the presence of an alkali metal molybdate in an inert atmosphere. In preparing the alkali metal salt of the dihydrocarbyl substituted dithiocarbamate, care must be exercised to accomplish the reaction at a pH within the range from about 7.5 to about 12. It is also important that the preparation of the alkali metal salt of the dihydrocarbyl substituted dithiocarbamate be completed in an atmosphere free of oxygen. In the acidification of the alkali metal salt of the dihydrocarbyl substituted dithiocarbamate, it is important that the pH be controlled within a range from about 3.5 to about 5.5. It is also important during this step that oxygen be excluded. As indicated more fully hereinafter, when extreme care is exercised in the acidification step, only the dihydrocarbyl substituted dithiocarbamate of molybdenum will be produced or at least the yield of the dimer and higher polymers thereof will be minimal and there will, generally, be no need to oxidize the product from this acidification step. It is, however, within the scope of the present invention to oxidize the product from the acidification step to convert any of the dimer back to the monomer using a suitable oxidizing agent such as a peroxide or hydroperoxide.

BRIEF DESCRIPTION OF THE DRAWING

The FIGURE is a schematic flow diagram of a process within the scope of the present invention.

DETAILED DESCRIPTION OF THE INVENTION

As indicated, supra, the present invention relates to an improved process for preparing dihydrocarbyl substituted dithiocarbamates of molybdenum. The preparation is completed in two steps. In the first step, an alkali metal hydroxide, a dihydrocarbyl substituted amine and carbon disulfide are reacted in an aqueous medium to produce an alkali metal salt of dithiocarbamate. In the second step, the alkali metal salt of dithiocarbamate is acidified in the presence of an alkali metal molybdate to produce a dihydrocarbyl substituted dithiocarbamate of molybdenum. When significant yields of the dihydrocarbyl substituted dithiocarbamate of molybdenum dimer are realized, the process may comprise a third step wherein the dimer is oxidized back to the monomer with a suitable oxidizing agent. In general, the alkali metal salt of dithiocarbamate from the first step will be separated from the aqueous reaction medium prior to acidification in the second step. Also, in general, a suitable solvent will be employed during the acidification. In processes proposed heretofore, the suitable solvent selected was one in which the desired product was soluble but wherein the tars and other impurities were not. Since, in the improved process of the present invention, these impurities are no longer produced, or at least not produced in significant quantities, a broader range of solvents may be used in the acidification step. In general, the same solvent used in the acidification step may be present in the third step when oxidation of any dimer product is either necessary or desirable.

In general, the alkali metal used as a hydroxide in the preparation of the alkali metal salt of the dithiocarbamate may be any of the metals of Group I of the Periodic Table of the Elements as published by Sargent Welch Scientific Company and copyrighted 1980. The process is, however, most effective when sodium as sodium hydroxide is used. As a a result, sodium hydroxide will be the preferred alkali metal hydroxide.

In general, the dihydrocarbyl substituted amine useful in the improved process of the present invention will have the general formula:

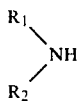

wherein:

$R_1$ and $R_2$ may be the same or different hydrocarbon radical selected from the group consisting of $C_1$-$C_8$ straight and branched chain aliphatic radicals; $C_5$-$C_8$ cycloalkyl radicals; alkyl substituted cycloalkyl radicals having from 1 to 3 carbon atoms in the alkyl group and from 5 to 7 carbon atoms in the cycloalkyl group; and aryl and alkylaryl radicals having from 1 to 4 carbon atoms in the alkyl portion thereof and 6 carbon atoms in the aryl portion thereof. $R_1$ and $R_2$ may also be a single cyclo or cylcoalkyl radical having from about 5 to about 10 carbon atoms.

In general, the alkali metal contained in the alkali metal molybdate used in the acidification step may be any of the alkali metals of Group I of the Periodic Table of Elements as published by Sargent Welch Scientific Company and copyrighted 1980. The process is, however, most effective when sodium molybdate is used and, as a result, sodium will be the preferred alkali metal.

In general, any oxidizing agent known to be effective for the breaking of a dimer of a dialkyl substituted dithiocarbamate of molybdenum may be used in the process of the present invention. Such oxidizing agents are well known in the prior art and include peroxides such as t-butylperoxide and hydroperoxides such as t-butylhydroperoxide and cumene hydroperoxide.

In accordance with the present invention, the dihydrocarbyl substituted amine and the carbon disulfide will be added to the aqueous rection media prior to adding the alkali metal hydroxide. The reactants will be combined, generally, in an inert atmosphere and particularly in the absence of air or oxygen. While the inventor does not wish to be bound by any particular theory, it is believed that the alkali metal salt of dithiocarbamate is unstable in the presence of air or oxygen and unstable in the presence of strong bases and in the presence of either or both decomposes to the corresponding dihydrocarbyl substituted thiouran disulfide and the alkali metal sulfide which in turn polymerizes to a mixture of polysulfides. This decomposition, in turn, reduces the amount of alkali metal salt of the dithiocarbamate available for acidification in the second step and leads to the production of by-products (impurities) which are not readily separable from the alkali metal salt of the dithiocarbamate. In accordance with this invention, it has been surprisingly discovered that this decomposition can be avoided or at least significantly reduced by excluding air or oxygen during the first step and by adding the alkali metal hydroxide after the dihydrocarbyl substituted amine and the carbon disulfide have been added to the aqueous reaction medium.

In general, the alkali metal salt of dithiocarbamate will be produced by reacting the alkali metal hydroxide, the dihydrocarbyl substituted amine and the carbon disulfide at a temperature within the range from about $-5°$ to about $30°$ C. Nominal contacting or holding times within the range from about 10 to about 240 minutes will be required to insure complete conversion of the reactant or reactants present in the least molar amounts. In general, equal molar amounts of all reactants will be combined although at least some conversion will occur when the reactants are combined in any molar ratios. Moreover, the use of a slight excess of carbon disulfide may increase the reaction rate. As indicated, supra, the pH of the reaction medium in the first step will be controlled within the range from about 7.5 to about 12.

In the second step of the process of the present invention, the alkali metal salt of dithiocarbamate, which will be obtained in high yield and high purity, is combined with an alkali metal molybdate and then acidified with the addition of a suitable acid. In general, any acid that will effectively adjust the pH to a value within the range from about 3.5 to about 3.5 may be employed. Suitable acids include acids such as nitric acid, hydrochloric acid, and sulfuric acid. The acid may be dissolved in water when added to the alkali metal salt of dithiocarbamate and the alkali metal molybdate. Similarly, the alkali metal molybdate may be dissolved in water when the same is added to or combined with the alkali metal salt of dithiocarbamate. In general, the alkali metal salt of dithiocarbamate will not be separated from the aqueous medium used in the first step. In general, the acidification accomplished in the second step will be accomplished at a temperature within the range from about $-5°$ to about $5°$ C. The acidification will be accomplished in an inert atmosphere and in the absence of oxygen or air. In general, the acidification will be accomplished by contacting the reactants at reaction conditions for a nominal holding time within the range from about 30 to about 500 minutes. By accomplishing the acidification within a relatively narrow temperature range and in the absence of oxidizing agents such as air and oxygen, the production of tars which has occurred in similar processes proposed heretofore is avoided. Moreover, and as indicated more fully hereinafter, controlling the temperature within an even narrower range than is broadly contemplated in the present invention will avoid or at least significantly reduce the yield of dihydrocarbyl substituted dithiocarbamate of molybdenum dimer and tars. As is known in the prior art, the tars heretofore produced during the acidification comprise a significant amount of the molybdenum added during the acidification step. Since the production of by-product (impurities) is eliminated or at least significantly reduced, it is not necessary in the improved process of the present invention to use an excess of alkali metal molybdate and, in fact, combination of reactants in stoichiometric amounts will result in high conversion of the alkali metal salt of dithiocarbamate to the corresponding dihydrocarbyl substituted dithiocarbamate of molybdenum.

The reactions occurring during the first and second steps of the improved process of this invention may be illustrated as follows:

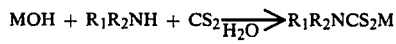

1.

$$R_1R_2NCS_2Na + M_2MoO_4 \xrightarrow{H^+} (R_1R_2NCS_2)_2MoO_2 + \underbrace{(R_1R_2NCS_2)_4Mo_2O_3}_{C} \quad 2.$$

wherein:

M is an alkali metal and $R_1$ and $R_2$ are as defined above.

When the conditions employed during acidification lead to significant yields of the dimer (identified as C in equation 2 above), the dimer may be oxidized back to the monomer by contacting the same with a suitable oxidizing agent such as a peroxide or hydroperoxide. In general, this may be accomplished by adding the oxidizing agent directly to the effluent from the second step.

In either case, that is the case wherein the reaction temperature during step 2 is controlled within a range so as to avoid the production of dimer or the case where the dimer is oxidized back to the monomer, the desired dihydrocarbyl substituted dithiocarbamate of molybdenum may be separated from the aqueous reaction medium by adding a suitable hydrocarbon solvent prior to, during or after the completion of the acidification. When this is done, the dihydrocarbyl substituted dithiocarbamate of molybdenum will dissolve in the solvent and may then be separated from the aqueous reaction medium by any suitable method known in the prior art such as decanting. In general, any of the solvents known in the prior art for dihydrocarbyl substituted dithiocarbamates of molybdenum may be used during the separation of the product from the process of the present invention. Such solvents include lower boiling aromatics and substituted aromatics such as benzene and toluene as well as halogenated hydrocarbons such as chloroform, dichloromethane and trichloromethane. The product may then be recovered from the solvent using any of the known suitable techniques such as distillation. Alternatively, the product could be separated from the solvent by precipitation with an anti-solvent followed by filtration or evaporation. In any case, the recovered product will be useful for any of the purposes known in the prior art including use as lubricant additives and soluble catalyst precursors for various hydrogenation reactions.

A continuous process within the scope of the present invention is illustrated in the attached FIGURE and it is believed that the invention will be better understood by reference to this FIGURE. Referring then to the FIGURE, a dihydrocarbyl substituted amine will be introduced into mixing vessel 100, preferably as an aqueous solution of said dihydrocarbyl substituted amine, through line 101 and combined with carbon disulfide introduced through line 102 and any additional water that may be required introduced through line 103. In general, the weight ratio of reactants to water in the first reactor 104 will be within the range from about 1:2 to about 1:100, on a weight basis. Sufficient water will then be added through line 103 to provide a ratio within this range giving due consideration to the amount of sodium hydroxide and any water combined therewith subsequently added. In the mixing vessel 100, the dihydrocarbyl amine and the carbon disulfide will be thoroughly mixed with the water. The mixing may be facilitated through the use of suitable means such as agitator 105.

The mixture is withdrawn from mixing vessel 100 through line 106—106 and passed to first reactor 104. An alkali metal hydroxide preferably as an aqueous solution thereof, will also be introduced into reactor 104 through line 107. An inert gas will also be introduced into reactor 104 through line 108. In general, reactor 104 will be operated at a temperature within the range from about −5° to about 30° C. In reactor 104, the dihydrocarbyl substituted amine, the carbon disulfide and the alkali metal hydroxide will react to produce an alkali metal salt of dithiocarbamate. The reaction is completed in an inert atmosphere due to the introduction of an inert gas through 108, which inert gas will be withdrawn through line 109 and may be recycled through line 108, though not illustrated. In general, any relative ratio of reactants may be employed but stoichiometric amounts of reactants will preferably be used so as to avoid the presence of unreacted reagents in the product.

The effluent from reactor 104 which will consist primarily of an aqueous solution of an alkali metal salt of dihydrocarbyl substituted dithiocarbamate will be withdrawn through lines 110—110 and passed to a second reactor 111. A stoichiometric amount of an alkali metal molybdate, preferably as an aqueous solution thereof, will be introduced into reactor 111 through line 112 and a sufficient amount of acid, preferably as a dilute aqueous solution thereof, to maintain a pH within the range from about 3.5 to about 5.5 in reactor 111 will be introduced through line 113. Also in a preferred embodiment, the stoichiometric amount of acid required to effect the acidification will be introduced through line 113. Reactor 111 will be operated at a temperature within the range from about −5° to about +5° C. In reactor 111 the alkali metal salt of dithiocarbamate and the alkali metal molybdate will be acidified to produce the corresponding dihydrocarbyl substituted dithiocarbamate of molybdenum. As indicated, supra, dimers of the dihydrocarbyl substituted dithiocarbamate of molybdenum may be formed but, at the conditions employed, there will be no significant production of the trimer or higher polymers thereof. In a preferred embodiment, an inert gas will also be introduced into reactor 111. Such an inert gas may be introduced through line 114 and withdrawn through line 115.

The effluent from reactor 111 which consists primarily of a mixture of a dihydrocarbyl substituted dithiocarbamate of molybdenum, in some cases the dimer thereof, and water is withdrawn through line 116 and passed to oxidizing vessel 117. In oxidizing vessel 117, the effluent is contacted with a suitable oxidizing agent, preferably a hydroperoxide and most preferably t-butylhydroperoxide, introduced through line 118. The oxidizing vessel will be operated such that any oxidation will be accomplished at a temperature within the range from about −5° to about 5° C. In the oxidizing vessel 117, any dimer of the dihydrocarbyl substituted dithiocarbamate of molybdenum will be oxidized to the monomer. The amount of oxidizing agent introduced through line 118 will, generally, be the stoichiometric amount to effect the desired oxidation or a slight excess thereover. However, when an oxidizing agent is used, it is important to wash the reaction mixture with water to remove any unused oxidizing agent. This step ensures stability of the product and prevents any undesirable oxidation which might take place upon the storage of the product.

The effluent from the oxidizing vessel will be withdrawn from oxidizing vessel 117 through line 119. In the embodiment illustrated, the effluent from the oxidizing vessel will be combined with a suitable solvent for the dihydrocarbyl substituted dithiocarbamate of molybdenum introduced through line 120 and then passed to suitable separating means 121 through line 122. As indicated, supra, and while the introduction of a suitable solvent has been illustrated after all reactions have been completed, the suitable solvent could have been introduced directly into reactor 111 or added to the effluent therefrom, though not illustrated. In the embodiment illustrated, a settling vessel has been illustrated as a suitable separating means. When such a means is employed, the settler must be properly sized to permit separation of the hydrocarbon phase and the water phase. The water will, of course, settle to the lower section of the vessel 123 and may be withdrawn through line 125. The hydrocarbon phase, on the other hand, which will comprise the dihydrocarbyl substituted dithiocarbamate of molybdenum will float to the upper portion of the vessel 124 and may be withdrawn through line 126. It will, of course, be appreciated that the aqueous phase withdrawn through line 125 could be recycled through line 103 to mixing vessel 100. The hydrocarbon phase, on the other hand, which is withdrawn through line 126 is then passed to a suitable separating means 127. In the embodiment illustrated, the suitable separating means is, simply, a flash drum wherein the solvent is flashed overhead and withdrawn through line 128 and the dihydrocarbyl substituted dithiocarbamate of molybdenum is withdrawn through line 129.

PREFERRED EMBODIMENT

In a preferred embodiment of the present invention, stoichiometric quantities of a dialkyl amine will be combined with carbon disulfide and water and thoroughly mixed. After the mixing is completed, a stoichiometric quantity of sodium hydroxide will be added to the thoroughly mixed mixture and reacted with the dialkyl amine and the carbon disulfide at a temperature within the range from about $-5°$ to about $30°$ C. The reactants will be maintained within this temperature range for a nominal holding time within the period from about 10 minutes to about 24 hours. In the preferred embodiment, the dialkyl amine may comprise the same or different alkyl groups, each having from about 1 to about 6 carbon atoms. The reaction of the dialkyl amine, carbon disulfide and the sodium hydroxide will be accomplished in an inert atmosphere and most preferably in the presence of nitrogen. The sodium salt of the dialkyl substituted dithiocarbamate thus produced will then be combined with a stoichiometric quantity of sodium molybdate and acidified with a dilute solution of nitric acid. The acidification will be accomplished at a temperature within the range from about $-5°$ to about $5°$ C. and in an inert atmoshere, most preferably in the presence of nitrogen. The nominal holding time during the acidification will be for a period of time within the range from about 30 to about 240 minutes. When the acidification is accomplished at a temperature within this relatively narrow range, the yield of dimer will be insignificant and it will not be necessary to use an oxidation step.

Having thus broadly described the present invention and a preferred embodiment thereof, it is believed that the same will become even more apparent by reference to the following examples. It will be appreciated, however, that the examples are presented solely for purposes of illustration and should not be construed as limiting the invention.

EXAMPLE 1

Into a stirred jacketed reactor were charged 130 gallons of water, 22.5 lbs. of NaOH, and 33.75 lbs. of N,N-butylamine. To the stirred reaction mixture, 2.1 gallons of $CS_2$ was added in portions. The mixture was stirred for 90 minutes longer and filtered directly into a storage tank.

From the solution of the dithiocarbamate as prepared above, 73 gallons of the soltuion was transferred into the reactor. The solution was associated with a brownish gummy oil. With stirring, 18.4 lbs. of sodium molybdate dihydrate and 33 gallons of water were added and the mixture was cooled with stirring to $0°-3°$ C. To the mixture, 205 lbs. of 7.3% aqueous nitric acid was added over 3 hours with stirring.

To the deep purple mixture, 10 gallons of toluene was added. The mixture was stirred for 30 minutes and the water layer from the bottom was discharged. Another 5 gallons of toluene and 50 gallons of water were added and the mixture was agitated for 30 minutes. The water layer was discharged. A significant amount of purple tar remained undissolved. The mixture was cooled, and 710 ml of t-butyl hydroperoxide was added in portions with stirring. After 1 hour, the color was still purple; two more portions of 350 ml of the hydroperoxide were added with continued stirring. Upon addition of 36 gallons of hexane, a purple yellowish brown liquid oiled out which was separated. On standing, the color further changed to brownish purple.

EXAMPLE 2

To a stirred mixture of 67.4 ml of dibutylamine and 1500 ml of water in a cooling bath inerted under $N_2$ were added 27 g of $CS_2$ and a solution of 17 g of NaOH in 500 ml of water. The mixture was stirred for 30 minutes longer and filtered to remove a small amount of solid. To this solution a cold solution of 70 g of $Na_2MoO_4.2H_2O$ in 1 liter water was added. Under $N_2$ and with constant stirring, a solution of 54.2 ml of $HNO_3$ in 400 ml of water was added slowly. To the mixture, 400 ml of toluene was added and stirring continued for 30 minutes. The mixture was allowed to settle and the bottom water layer was siphoned off. To the cooled clear purple solution at $0°-3°$ C., 6 ml of t-butylhydroperoxide was added and after 30 minutes the orange yellow solution was transferred to separatory funnel, washed two times with water, dried over Drierite and diluted with 1200 ml of petroleum ether and allowed to stand overnight. The yellow crystalline product was collected, the m.p. of the product was $69.5°-70.5°$ C.

EXAMPLE 3

To a stirred mixture of 33.75 lbs of dibutylamine and 130 gallons of water at $0°-5°$ C. inerted under $N_2$ were added 2.1 gallons of $CS_2$ followed by 22.5 lb of NaOH. The mixture was stirred at $0°-5°$ C. for 2 hours and then filtered to remove a very small amount of solid. The solution was transferred to the reactor, blanketed with $N_2$ and stirred at $0°-3°$ C. while 36 lbs of $Na_2Mo_42H_2O$ in 60 gallons of water were added. To the stirred mixture 400 lbs of 7.3% aqueous nitric acid was added slowly while maintaining the temperature at $0°-3°$ C. and under a steady flow of $N_2$. After 2 hours, 25 gallons of toluene were added and stirring was continued for 1.5 hours more. After allowing the reaction mixture to stand overnight, the bottom water layer was removed and to the mixture was added 50 gallons of hexane. The resulting yellow solid which separated out was collected and dried, m.p., 69°–70° C. No t-butylhydroperoxide was used.

Anal. calculated for $C_{18}H_{36}N_2O_2S_4Mo$: C, 40.28; H, 6.76; N, 5.22; Mo, 17.88; Found: C, 40.05; H, 6.75; N, 5.18; Mo, 17.98

As is clear from the example given, the modifications of this invention consisting of an inverse addition of NaOH to the amine and $CS_2$ in water, (2) maintaining an inert atmosphere, and (3) proper control of the environment lead to significant improvement of the process and are essential for the preparation of the desired product.

While the present invention has been described and illustrated by reference to particular embodiments thereof, it will be appreciated by those of ordinary skill in the art that the same lends itself to variations not necessarily illustrated herein. For this reason, then, reference should be made solely to the appended claims for purposes of determining the true scope of the present invention.

Having thus described and illustrated the invention, what is claimed is:

1. A method for preparing a dihydrocarbyl substituted dithiocarbamate of molybdenum comprising the steps of:
   (a) adding an alkali metal hydroxide to a mixture of a dihydrocarbyl substituted amine, carbon disulfide and water and allowing the alkali metal hydroxide, the dihydrocarbyl substituted amine and the carbon disulfide to react to produce an alkali metal salt of a dihydrocarbyl substituted ditiocarbamate in an inert atmosphere and at a temperature within the range from about $-5°$ to about 30° C.;
   (b) combining at least a portion of the alkali metal salt of the dihydrocarbyl substituted dithiocarbamate from step (a) with an alkali metal molybdate and acidifying the resulting combination at a pH within the range from about 3.5 to about 5.5 in an inert atmosphere and at a temperature within the range from about $-5°$ to about 5° C. to produce a dihydrocarbyl substituted dithiocarbamate of molybdenum; and
   (c) recovering a dihydrocarbyl substituted dithiocarbamate of molybdenum.

2. The process of claim 1 wherein the product from step (b) is contacted with an oxidizing agent before the dihydrocarbyl substituted dithiocarbamate of molybdenum is recovered.

3. The process of claim 2 wherein said alkali metal hydroxide is sodium hydroxide.

4. The process of claim 2 wherein said alkali metal molybdate is sodium molybdate.

5. The process of claim 1, wherein each of the dihydrocarbyl substitutions on said dihydrocarbyl substituted amine is the same or a different hydrocarbon radical selected from the group consisting of $C_1$–$C_8$ straight and branched chain aliphatic radicals; $C_5$–$C_8$ cycloalkyl radicals; alkyl substituted cycloalkyl radicals having from 1 to 3 carbon atoms in the alkyl group and from 5 to 7 carbon atoms in the cycloalkyl group; and aryl and alkylaryl radicals having from 1 to 4 carbon atoms in the alkyl portion thereof and 6 carbon atoms in the aryl portion thereof or constitute a single cyclo or cycloalkyl radical having from about 5 to about 10 carbon atoms.

* * * * *